(12) United States Patent
Brownhill et al.

(10) Patent No.: US 11,633,297 B2
(45) Date of Patent: Apr. 25, 2023

(54) TOTAL ANKLE EXTERNAL ALIGNMENT FOOTPLATE

(71) Applicant: Zimmer, Inc., Warsaw, IN (US)

(72) Inventors: Sarah Brownhill, Warsaw, IN (US); Brian K. Berelsman, Warsaw, IN (US); Sandra Snyder, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 956 days.

(21) Appl. No.: 16/510,145

(22) Filed: Jul. 12, 2019

(65) Prior Publication Data

US 2020/0015992 A1  Jan. 16, 2020

Related U.S. Application Data

(60) Provisional application No. 62/697,229, filed on Jul. 12, 2018.

(51) Int. Cl.
| *A61F 5/01* | (2006.01) |
| *A61F 2/76* | (2006.01) |
| *A61B 17/02* | (2006.01) |
| *A61F 2/30* | (2006.01) |
| *A61F 2/66* | (2006.01) |
| *A61B 17/90* | (2006.01) |
| *A61B 90/00* | (2016.01) |

(52) U.S. Cl.
CPC .......... *A61F 5/0111* (2013.01); *A61B 17/025* (2013.01); *A61F 2/76* (2013.01); *A61B 17/90* (2021.08); *A61B 2090/067* (2016.02); *A61B 2090/0811* (2016.02); *A61B 2090/3983* (2016.02); *A61F 2/6607* (2013.01); *A61F 2002/30433* (2013.01); *A61F 2002/30462* (2013.01)

(58) Field of Classification Search
CPC combination set(s) only.
See application file for complete search history.

(56) References Cited

U.S. PATENT DOCUMENTS

2012/0271314 A1* 10/2012 Stemniski .......... A61B 17/1739
606/87

* cited by examiner

*Primary Examiner* — Sameh R Boles
(74) *Attorney, Agent, or Firm* — Schwegman Lundberg & Woessner, P.A.

(57) ABSTRACT

A footplate assembly for ankle includes a footplate base; a slider arm that is rotatably coupled to the footplate base, the slider arm being configured to be couplable to external ankle instrumentation; a locking fastener configured to lock the slider arm in a chosen orientation relative to the footplate base; and a knob coupled to the footplate base having a scale to display the angle of the slider arm relative to the footplate base.

17 Claims, 5 Drawing Sheets

TOTAL ANKLE EXTERNAL ALIGNMENT FOOTPLATE

CLAIM OF PRIORITY

This application claims the benefit of U.S. Provisional Patent Application Ser. No. 62/697,229, filed on Jul. 12, 2018, the benefit of priority of which is claimed hereby, and which is incorporated by reference herein in its entirety.

FIELD

The present subject matter relates generally to orthopedic surgical devices, and more specifically to ankle orthopedic devices.

BACKGROUND

Current total ankle systems using external alignment instrumentation require the surgeon to hold the foot with one hand, while setting alignment of the tibia and talus resections with the other hand. For example, talar instrumentation is positioned and locked into place while the surgeon holds the foot in the correct alignment compared to the tibia. This can result in improper alignment and is hard to replicate during a procedure.

OVERVIEW

Example 1 can include subject matter that can include a footplate assembly for ankle surgery. The footplate assembly includes a footplate base; a slider arm that is rotatably coupled to the footplate base, the slider arm being configured to be couplable to external ankle instrumentation; a locking fastener configured to lock the slider arm in a chosen orientation relative to the footplate base; and a knob coupled to the footplate base having a scale to display the angle of the slider arm relative to the footplate base.

In Example 2, the subject matter of Example 1 can optionally include the footplate base defining generally planar upper and lower surfaces and extends from an upper end to a lower end defining a longitudinal axis.

In Example 3, the subject matter of any of Examples 1-2 can optionally include the slider arm being rotatably coupled to a side of the footplate base proximate a middle portion of the footplate base.

In Example 4, the subject matter of any of Examples 1-3 can optionally include the knob being fixed to the footplate base such that the knob does not rotate relative to the footplate base and does rotate relative to the slider arm.

In Example 5, the subject matter of Example 4 can optionally include the scale including a plurality of degree markings on an outer surface of the knob.

In Example 6, the subject matter of any of Examples 1-5 can optionally include the locking fastener being received within an end of the knob to lock the slider arm.

In Example 7, the subject matter of any of Examples 1-6 can optionally include a footplate arm configured to slideably receive the slider arm.

In Example 8, the subject matter of Example 7 can optionally include the footplate arm including a first leg couplable to the external ankle instrumentation and a second leg perpendicular to the first leg to slideably receive the slider arm.

In Example 9, the subject matter of any of Examples 1-8 can optionally include the slider arm including a generally square-shaped cross-section and the second leg includes a generally square shaped cross-section to receive the slider arm.

In Example 10, the subject matter of any of Examples 1-9 can optionally include the footplate base including one or more fluoroscopy targets.

Example 11 can include subject matter that can include a footplate assembly for ankle surgery. The footplate assembly including a footplate base; a slider arm that is rotatably coupled to the footplate base, the slider arm being configured to be couplable to external ankle instrumentation; a locking fastener configured to lock the slider arm in a chosen orientation relative to the footplate base; and a footplate arm configured to slideably receive the slider arm.

In Example 12, the subject matter of Example 11 can optionally include the footplate arm including a first leg couplable to the external ankle instrumentation and a second leg perpendicular to the first leg to slideably receive the slider arm such that the second leg of the footplate arm and the slider arm are both generally parallel to a longitudinal axis of the external ankle instrumentation.

In Example 13, the subject matter of Example 12 can optionally include the slider arm including a generally square-shaped cross-section and the second leg includes a generally square shaped cross-section to receive the slider arm.

In Example 14, the subject matter of any of Examples 11-13 can optionally include the slider arm being movable proximally or distally relative to the footplate arm as needed by the surgeon.

In Example 15, the subject matter of any of Examples 11-14 can optionally include a fastener to rigidly fasten the relative position of the slider arm to the footplate arm and including a knob coupled to the footplate base having a scale to display the angle of the slider arm relative to the footplate base.

In Example 16, the subject matter of Example 15 can optionally include the knob being fixed to the footplate base such that the knob does not rotate relative to the footplate base and does rotate relative to the slider arm, and wherein the scale includes a plurality of degree markings on an outer surface of the knob.

In Example 17, the subject matter of any of Examples 11-16 can optionally include the slider arm being movable anteriorly or posteriorly relative to the footplate arm as needed by the surgeon.

Example 18 can include subject matter that can include a method adjusting a footplate assembly for ankle surgery. The method including rotatably coupling a slider arm to a footplate base; coupling the slider arm to external ankle instrumentation; rotating the footplate base relative to the slider arm until a desired angle orientation is achieved; and fastening a locking fastener to lock the slider arm in the chosen angle orientation relative to the footplate base.

In Example 19, the subject matter of Example 18 can optionally include a knob coupled to the footplate base and having a scale to display the angle of the slider arm relative to the footplate base.

In Example 20, the subject matter of any of Examples 18-19 can optionally include a footplate arm configured to slideably receive the slider arm, wherein the footplate arm includes a first leg couplable to the external ankle instrumentation and a second leg perpendicular to the first leg to slideably receive the slider arm.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
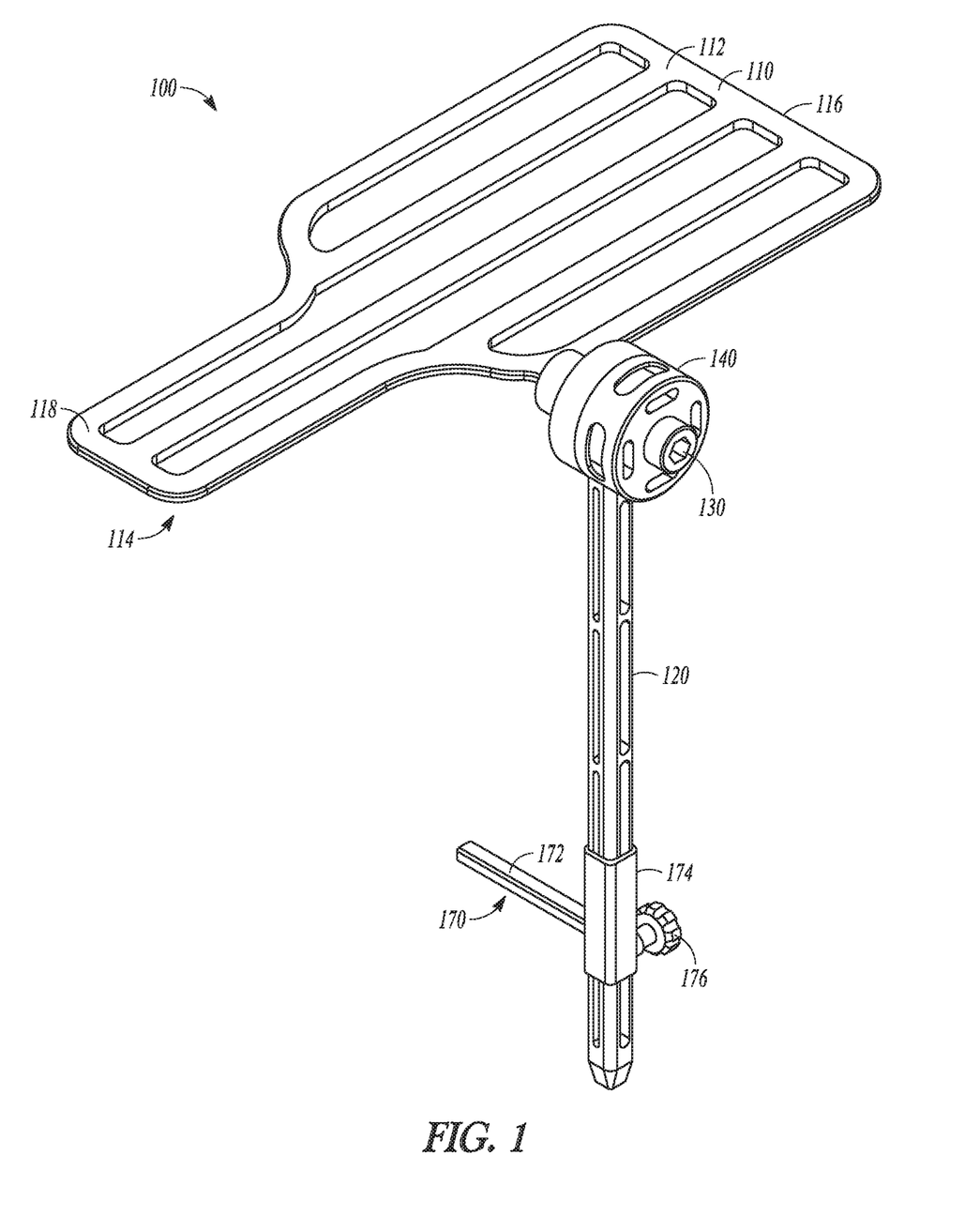
FIG. 1 shows an isometric view of a footplate assembly, in accordance with one embodiment.
Figure 2:
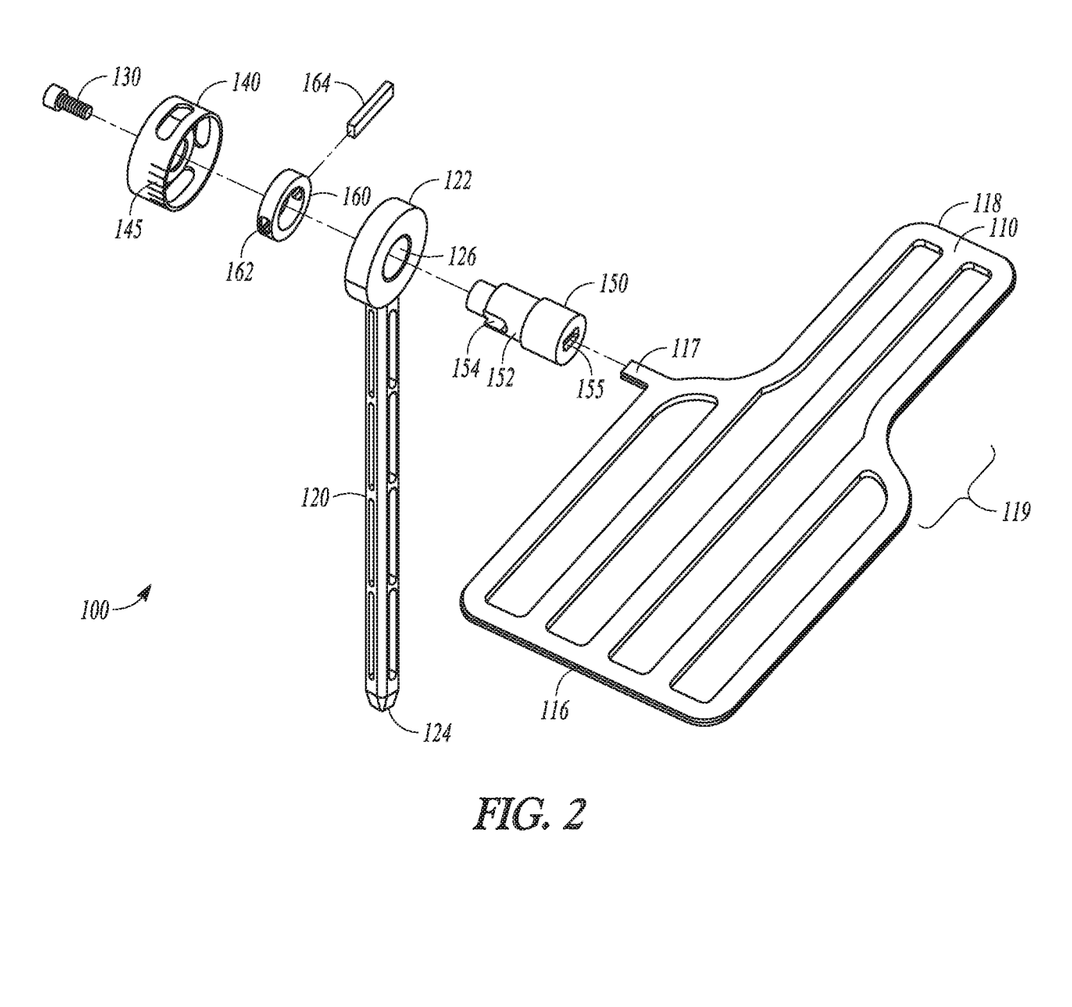
FIG. 2 shows an exploded view of the footplate assembly of FIG. 1, in accordance with one embodiment.
Figure 3:
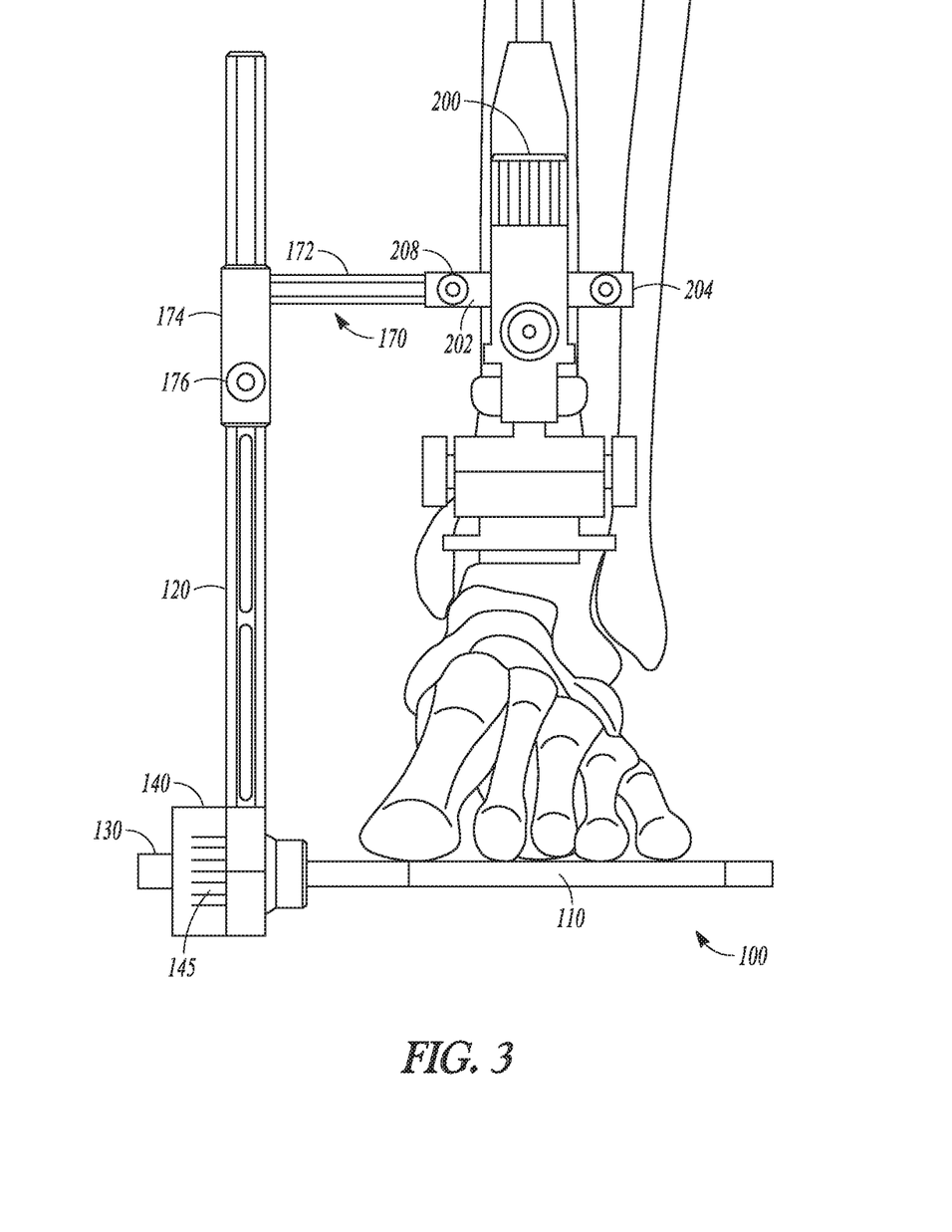
FIG. 3 shows a front view of the footplate assembly of FIG. 1, in accordance with one embodiment.

FIG. 1 shows footplate assembly 100 for ankle joint replacement surgery. FIG. 2 shows an exploded view of footplate assembly 100. The footplate assembly 100 generally includes a footplate base 110 and a slider arm 120 that is rotatably coupled to the footplate base 110. The slider arm 120 can be configured to be couplable to external ankle instrumentation 200 (FIG. 3). A locking fastener 130 can be configured to lock the slider arm 120 in a chosen orientation relative to the footplate base 110. A knob 140 can be coupled to the footplate base 110. The knob 140 can include a scale 145 to display an angle of the slider arm 120 relative to the footplate base 110.

The footplate base 110 defines generally planar upper and lower surfaces 112, 114 and extends from an upper end 116 to a lower end 118 defining a longitudinal axis. The footplate base 110 can include a wider upper end 116 for the forefoot and a narrower lower end 118 for the hindfoot.

The slider arm 120 is rotatably coupled to a side of the footplate base 110 proximate a middle portion 119 of the footplate base 110 between the upper and lower ends 116, 118. The slider arm 120 can include a square shaped cross-section bar extending from a first end 122 to a second end 124 defining a longitudinal axis and the first end 122 can be rotatably coupled to the footplate base 110. In other examples the slider arm 120 can have a rectangular cross-section or a triangular or circular cross-section.

The knob 140 is coupled to the footplate base 110 such that the knob 140 does not rotate relative to the footplate base 110 and does rotate relative to the slider arm 120. The scale 145 includes a plurality of degree markings on an outer surface of the knob 140. The knob 140, located on the side of the footplate base 110, includes the degree markings of scale 145 to indicate the degree of flexion or plantar flexion of the footplate base 110 to the long axis of the tibia. Using the footplate locking fastener 130, the surgeon can lock the footplate base 110 into the desired angle.

A connection member 150 having a generally cylindrical body is fastened to the mid portion 119 of the footplate base 110 at a connection projection 117 and an end 122 of the slider arm 120 includes a hole 126 that is dimensioned to be received by at least a portion of the cylindrical body of the connection member 150.

A ring 160 can be located over the connection member 150 and is fastened by a ring plate 164 to the connection member 150 such that the slider arm 120 is sandwiched between a shoulder 152 on the connection member 150 and the ring 160. The ring plate 164 goes through cutout slots 162 in the ring 160 aligned with a cut-out slot 154 in the connection member 150. An end 155 of the connection member 150 is attached to the side of the footplate base 110. The connection member 150 includes the cut-out slot 154 to receive the ring plate 164 to loosely fasten the ring 160 to the connection member 150. The cut-out slot 154 is dimensioned to allow the ring 160 to move back and forth so that the slider arm 120 freely rotates until the locking fastener 130 is tightened to lock everything in place.

The locking fastener 130 is received within an end of the knob 140 and enters into internal threads in the connection member 150 to lock the slider arm 120 between the ring 160 and the shoulder 152. The slider arm 120 is thereby squeezed between the shoulder 152 and the ring 160 so as to be frictionally held in place. The locking fastener 130 can be a screw received within corresponding internal threads extending within a longitudinal axis of the connection member 150.

Current external alignment systems do not include instrumentation to accurately set the flexion/extension position of the talus compared to the tibial resection. Flexion/extension of the talus to the tibia is currently set by the surgeon visually positioning the foot perpendicular to the long axis of the tibia. To apply additional degrees of flexion/extension to the talar resection compared to the tibia, the surgeon will set the angle of the foot by eye and will hold the foot in the angled position while locking the instrumentation into place. Additionally, it is difficult for the surgeon to replicate the same flexion/extension position of the talus to the tibia during various steps in the procedure.

Without an instrument to set the rotation/position of the talus to the tibia and hold the foot in the correct alignment and degree of flexion, inaccuracies in the bone resections and soft tissue alignment may occur.

Here, the footplate assembly 100 sets accurate degrees of flexion/extension or plantar flexion/dorsi flexion between the tibia and the foot. The surgeon can accurately set the foot at 90 degrees to the long axis of the tibia, or the surgeon may choose to apply additional flexion/extension or plantar flexion/dorsi flexion to the talar resection.

Figure 4:
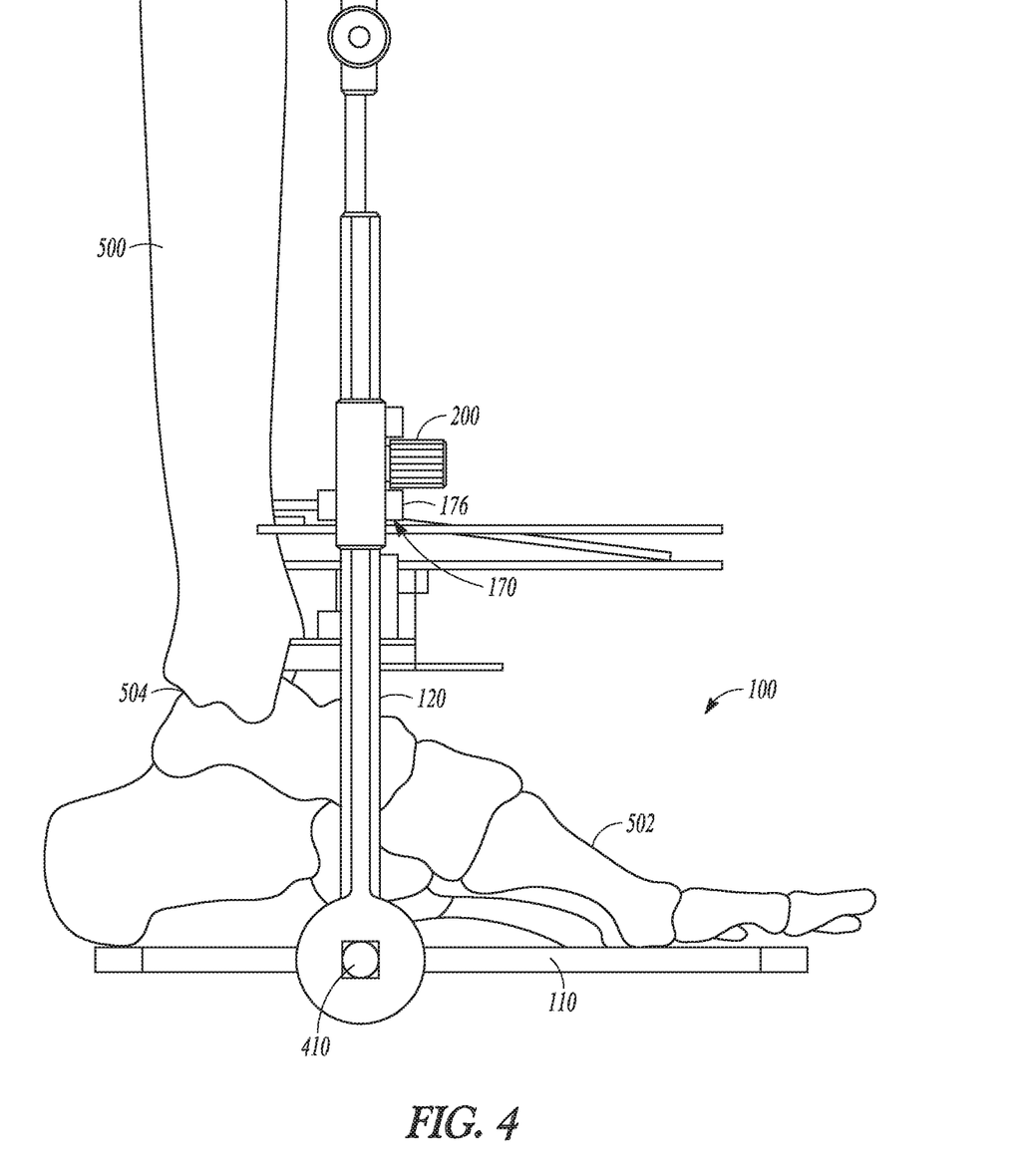
FIG. 4 shows a side view of the footplate assembly of FIG. 1, in accordance with one embodiment.

Referring also now to FIGS. 3 and 4, which show front and side views of the footplate assembly 100. The footplate assembly is attached to external ankle instrumentation 200, such as alignment instrumentation, to allow proper alignment of a tibia 500 and talus 504 of a foot 502.

In one embodiment, a footplate arm 170 can be configured to slidably receive the slider arm 120. The footplate arm 170 includes a first leg 172 couplable to the external ankle instrumentation 200 and a second leg 174 perpendicular to the first leg 172 to slidably receive the slider arm 120, such that the second leg 174 of the footplate arm 170 and the slider arm 120 are both generally parallel to a longitudinal axis of the external ankle instrumentation 200. The slider arm 120 includes a generally square-shaped cross-section and the second leg 174 includes a corresponding generally square shaped cross-section to receive the slider arm 120.

The slider arm 120 can be moved proximally or distally relative to the footplate arm 170 (and thus the external ankle instrumentation 200) as needed by the surgeon. There is a bolt or other fastener 176 to rigidly fasten the relative position of the slider arm 120 to the footplate arm 170. Moreover, this allows the footplate assembly 100 to be quickly removed from the instrumentation 200 while still holding the desired angle of the footplate base 110 and the slider arm 120. This helps allow for replication of the angle during a surgical procedure.

Current total ankle systems with intramedullary alignment that include a foot holder are cumbersome and increase surgical time. The foot plate cannot be removed from the large foot holder frame. Therefore, it can interfere with adjustability required during various parts of the procedure. Requiring a large frame foot holder to perform a total ankle procedure instead of a separate foot plate may increase the complexity of the surgery and limit adjustability.

In the present system, in one or more embodiments discussed herein, the footplate assembly 100 can be attached to the external alignment instrumentation 200 and removed as required during the surgery.

The external alignment instrumentation 200 attaches to the footplate assembly 100 by the footplate arm 170. The footplate arm 170 assembles into a square boss 202, 204 on either side of the external alignment guide 200 and is locked into position with a bolt 208. The square boss 202, 204 ensures leg 172 of the footplate arm 170 is perpendicular to the external alignment guide 200 and the leg 174 is parallel thereto.

The slider arm 120 can include a square shaped cross-section and attaches to the footplate arm 170 through a squared hole on the footplate arm 170. The mating square shape on the slider arm 120 and the squared thru hole on the footplate arm 170 ensures the slider arm 120 is parallel to a longitudinal axis of the external alignment guide 200. The slider arm 120 can slide through the footplate arm 170 hole to accommodate various patient heights and bone sizes. Thus, the footplate assembly 100 can help to apply compression or distraction to the joint throughout the procedure.

One or more fluoroscopy targets 410 can also be added to the base 110 of the footplate assembly 100 to assist with alignment and positioning of the talus compared to the tibia, defining talar sizing, or depth of the talar resection, and defining the arc center of the talar dome. Defining the arc center of the talar dome, and plantar flexing or dorsi flexing the talus, using the footplate assembly 100, around this point, will help to maintain natural kinematics of the joint and provide additional accuracy of the talar bone resections and placement of the talar implant.

External alignment systems currently on the market do not provide a method to set the initial position of the talar resections based on the talar dome radius of curvature. The talar dome radius of curvature helps to define the talar size and the center of the talar dome radius of curvature helps to define the rotational motion of the talus. Including a method to determine the talar dome radius of curvature increases the accuracy of the talar bone resections and talar implant sizing based on the patient's anatomy.

Here the footplate fluoroscopy targets 410 can define the position of the center of the talar dome radius of curvature, and the size of the talar dome radius of curvature, prior to any bone cuts.

Figure 5:
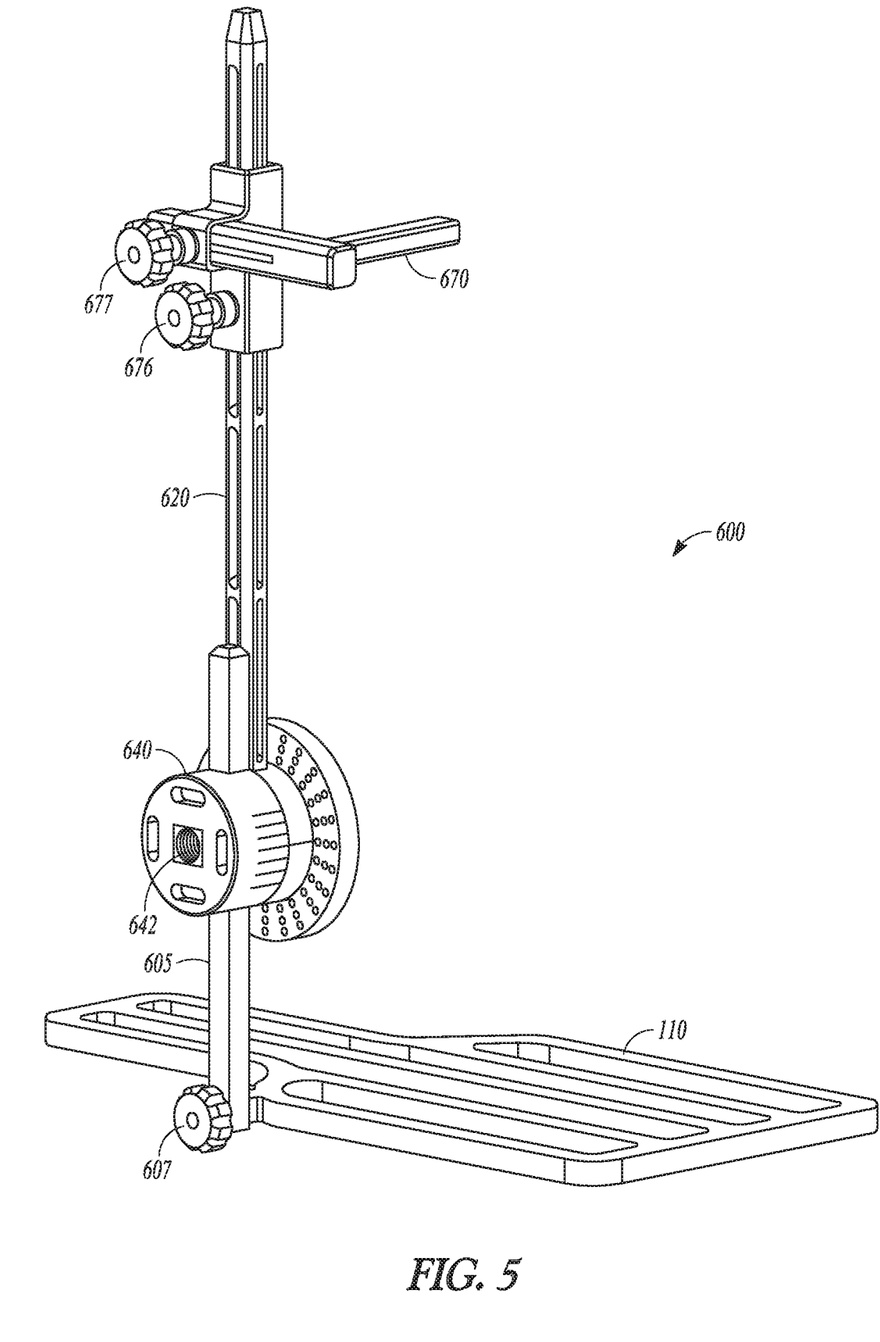
FIG. 5 shows an isometric view of a footplate assembly, in accordance with one embodiment.

FIG. 5 shows a footplate assembly 600 according to one embodiment. Footplate assembly 600 includes many similarities with footplate assembly 100 and certain details will be omitted for sake of brevity. Footplate assembly 600 generally includes the footplate base 110 coupled to a first arm 605 by a fastener 607. A knob 640 including angle degree markings is coupled to first arm 605. A slider arm 620 is rotatably coupled to the knob 640. A locking fastener 130 (FIG. 1) can be inserted into a threaded hole 642 to lock the relative positions of the base 110 and the slider arm 620. A footplate arm 670 can slideably receive slider arm 620 and can be fastened thereto by a fastener 676. The footplate arm 670 can be attached to external instrumentation. Another arm can be slideably coupled to slider arm 620 or footplate arm 670 to allow the slider arm 620 to be moved anteriorly or posteriorly relative to the footplate arm as needed by the surgeon.

To use the footplate assembly 100 (or 600), the slider arm 120 is coupled to the footplate base 110. The footplate base 110 is rotated relative to the slider arm 120 until a desired angle orientation is achieved. The locking fastener 130 is fastened to lock the slider arm 120 in the chosen angle orientation relative to the footplate base 110. As noted, the knob 140 can be coupled to the footplate base 110 and include the scale 145 to display the angle of plantarflexion/dorsiflexion.

The slider arm 120 can be coupled to the external ankle instrumentation 200. After locking the footplate base 110 into the correct angle, the slider arm 120 can be slid further through the square cutout on the footplate arm 170, and the bottom of the footplate assembly base can be pressed securely against the patient's foot and locked into position with a bolt 176. Once the footplate arm 170, slider arm 120 and the footplate base 110 are locked, the angle of the talus to the tibia can be securely positioned, allowing the surgeon to set other instrumentation and accurately prepare a talar resection, for example.

The footplate assembly 100 includes adjustability for patient anatomy, surgical technique, and surgeon preference. The angle of the footplate base 110, and therefore the angle of the talus 504 to the tibia 500, can be adjusted by loosening the footplate locking fastener 130 and rotating the footplate base 110. Compression, applied to the ankle joint by compressing the footplate base 110 to the bottom of the patient's foot, may be adjusted by loosening the footplate sliding arm bolt 176, and sliding the sliding arm 120 proximal and distal along the footplate arm 170.

Using a surgical wrap to secure the patients toes to the top of the footplate base 110, the surgeon may loosen the footplate assembly 100 and distract the joint while maintaining the correct plantar flexion/dorsi flexion or flexion/extension. When the footplate base 110 is not locked into place with the footplate locking fastener 130 the footplate base 110 is free to spin around the footplate arm 120 at 360 degrees, allowing the footplate assembly 100 to be used on either a right or left foot.

The present system provides many advantages over former systems. For example, in one or more embodiments, the footplate assembly 100 can be attached to the medial side or lateral side of the external alignment instrumentation 200, based on surgeon preference or patient ankle. The footplate assembly 100 allows the surgeon to set the position of the talar bone 504 to the tibia 500 and hold this position while locking the tibial instrumentation 200 into place. The footplate assembly 100 holds the foot in the correct position and frees up both of the surgeon's hands to perform the next steps in the procedure. The footplate assembly 100 holds the foot in the correct position and maintains this position throughout various steps in the procedure. The footplate assembly 100 or portions thereof, for example, just the footplate base 110 and the slider arm 120, can be attached to or removed from the external alignment guide 200 at any point throughout the surgery. The footplate assembly 100 includes adjustability for the height of the patient and/or anterior/posterior position of the joint center and/or width of the patient's foot.

In an example, the footplate assembly 100 increases the alignment accuracy of a talar bone resection. The surgeon can set the alignment of the talus to the tibia and hold this alignment in place while making bone resections. The surgeon is also able to move between steps in the surgical technique and ensure the alignment of the talus to the tibia has been maintained. The footplate assembly also enables the surgeon to plantar flex or dorsi flex the talus bone at a defined angle, compared to the tibia, and make a straight cut at a defined depth. Creating a straight cut decreases the risk of skiving off of the domed talar bone, therefore increasing the accuracy of the cut.

Plantar flexing or dorsi flexing the foot to make a first angled cut, without an initial flat cut to use as a datum, reduces the amount of talar bone resection. For example, preparing for a 2-chamfer talar implant design with a 20-degree posterior chamfer, the talus would be plantar flexed using the footplate assembly at 20 degrees. The first cut of the talar bone would be resected using a straightcut through instrumentation attached to the external alignment guide. By plantar flexing the talar bone using the footplate assembly 100, the posterior resection would accurately match the posterior chamfer of the talar implant. Once an initial resection is made, the additional resections can be defined directly from the first cut. Without plantar flexing the foot, a 20-degree resection would have been necessary. Defining the start point of the angled resection and avoiding other patient anatomy, makes an angled first-cut challenging.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. A footplate assembly for ankle surgery, comprising:
a footplate base;
a slider arm that is rotatably coupled to the footplate base, the slider arm being configured to be couplable to external ankle instrumentation;
a locking fastener configured to lock the slider arm in a chosen orientation relative to the footplate base; and
a knob coupled to the footplate base having a scale to display the angle of the slider arm relative to the footplate base.

2. The footplate assembly of claim 1, wherein the footplate base defines generally planar upper and lower surfaces and extends from an upper end to a lower end defining a longitudinal axis.

3. The footplate assembly of claim 1, wherein the slider arm is rotatably coupled to a side of the footplate base proximate a middle portion of the footplate base.

4. The footplate assembly of claim 1, wherein the knob is fixed to the footplate base such that the knob does not rotate relative to the footplate base and does rotate relative to the slider arm.

5. The footplate assembly of claim 4, wherein the scale includes a plurality of degree markings on an outer surface of the knob.

6. The footplate assembly of claim 1 wherein the locking fastener is received within an end of the knob to lock the slider arm.

7. The footplate assembly of claim 1 further including a footplate arm configured to slideably receive the slider arm.

8. The footplate assembly of claim 7, wherein the footplate arm includes a first leg couplable to the external ankle instrumentation and a second leg perpendicular to the first leg to slidably receive the slider arm.

9. The footplate assembly of claim 8, wherein the slider arm includes a generally square-shaped cross-section and the second leg includes a generally square shaped cross-section to receive the slider arm.

10. The footplate assembly of claim 1, wherein the footplate base includes one or more fluoroscopy targets.

11. A footplate assembly for ankle surgery, comprising:
a footplate base;
a slider arm that is rotatably coupled to the footplate base, the slider arm being configured to be couplable to external ankle instrumentation;
a locking fastener configured to lock the slider arm in a chosen orientation relative to the footplate base; and
a footplate arm configured to slideably receive the slider arm.

12. The footplate assembly of claim 11, wherein the footplate arm includes a first leg couplable to the external ankle instrumentation and a second leg perpendicular to the first leg to slidably receive the slider arm such that the second leg of the footplate arm and the slider arm are both generally parallel to a longitudinal axis of the external ankle instrumentation.

13. The footplate assembly of claim 12, wherein the slider arm includes a generally square-shaped cross-section and the second leg includes a generally square shaped cross-section to receive the slider arm.

14. The footplate assembly of claim 13, wherein the slider arm can be moved proximally or distally relative to the footplate arm as needed by the surgeon.

15. The footplate assembly of claim 14, including a fastener to rigidly fasten the relative position of the slider arm to the footplate arm and including a knob coupled to the footplate base having a scale to display the angle of the slider arm relative to the footplate base.

16. The footplate assembly of claim 15, wherein the knob is fixed to the footplate base such that the knob does not rotate relative to the footplate base and does rotate relative to the slider arm, and wherein the scale includes a plurality of degree markings on an outer surface of the knob.

17. The footplate assembly of claim 14, wherein the slider arm can also be moved anteriorly or posteriorly relative to the footplate arm as needed by the surgeon.

\* \* \* \* \*